United States Patent [19]

Gross

[11] Patent Number: 5,556,703

[45] Date of Patent: Sep. 17, 1996

[54] ABSORBENT PHYCOCOLLOIDS AND A METHOD FOR THEIR MANUFACTURE

[75] Inventor: James R. Gross, Appleton, Wis.

[73] Assignee: Kimberly-Clark Corporation, Neenah, Wis.

[21] Appl. No.: 448,062

[22] Filed: May 23, 1995

Related U.S. Application Data

[63] Continuation of Ser. No. 977,459, Nov. 18, 1992.

[51] Int. Cl.$^6$ ....................................................... B32B 1/00
[52] U.S. Cl. ........................ 428/402; 428/402.24; 536/3; 525/54.3
[58] Field of Search ................. 427/213.33; 428/402.24, 428/402; 536/3; 525/54.3

[56] References Cited

U.S. PATENT DOCUMENTS

| | | | |
|---|---|---|---|
| Re. 32,649 | 4/1988 | Brandt et al. ............................ | 604/368 |
| 4,446,261 | 5/1984 | Yamasaki et al. ......................... | 524/40 |
| 4,824,916 | 4/1989 | Kershner et al. ......................... | 525/420 |

*Primary Examiner*—Jeffrey Mullis
*Attorney, Agent, or Firm*—Thomas J. Mielke

[57] ABSTRACT

Described is a method for preparing a water-swellable, substantially water-insoluble material. The method involves forming a first solution containing a water-soluble phycocolloid. The first solution is then added to a second solution containing an ion capable of rendering the water-soluble phycocolloid substantially water insoluble. The phycocolloid material is then removed from the second solution and subjected to a solvent exchange to remove water present in the phycocolloid material. Hollow particles can be formed by including a gelation-retarding agent in the first solution. Also described is a water-swellable, substantially water-insoluble particle defining an interior void. The particle comprises an outer shell formed from a water-insoluble phycocolloid. The outer shell defines an interior void which contains a phycocolloid.

4 Claims, No Drawings

ABSORBENT PHYCOCOLLOIDS AND A METHOD FOR THEIR MANUFACTURE

BACKGROUND OF THE INVENTION

This is a continuation of copending U.S. patent application Ser. No. 07/977,459, filed Nov. 18, 1992.

1. Field of the Invention

The present invention relates to absorbent materials and their method of manufacture. Specifically, the present invention relates to absorbent materials formed from phycocolloids.

2. Description of the Related Art

The term "phycocolloid" refers to one of several carbohydrate polymers (polysaccharides) occurring in algae and moss. Phycocolloids are hydrophilic colloids having a tendency to absorb water and to form gels of varying strengths and consistency. The chief types of phycocolloids are carrageenan from Irish moss, algin from brown algae, and agar from red algae. Many uses for phycocolloids such as algin are known. The book titled *Industrial Gums, Polysaccharides and Their Derivatives,* edited by Roy L. Whistler (Academic Press, Second Edition, 1973), indicates that the use of algin is indicated whenever thickening, suspending, emulsifying, stabilizing, and gel-forming applications are involved. Algins are said to have found use in food products, pharmaceuticals and cosmetics, paper products, textile products, rubber products, and a number of other industrial uses.

The gel-Forming properties of phycocolloids have resulted in the use of some phycocolloids in absorbent applications. U.S. Pat. No. 3,653,383 issued Apr. 4, 1972, to Wise describes an algin sponge. Disclosed is a water-absorbent and water-disintegrative open-celled porous algin sponge. The sponge is said to be useful as a medical receptor for biological fluids. The process of manufacture involves freezing an algin dispersion, such as a gel of sodium alginate and calcium alginate, and thereafter sublimating the frozen dispersion medium. Similarly, U.S. Pat. No. 4,090,013 issued May 16, 1978, to Ganslaw et al. is directed to an absorbent composition of matter. Described is a dry, water-swellable, water-insoluble absorbent composition of matter. The absorbent composition comprises an ionic complex of a water-soluble anionic polyelectrolyte and a polyvalent metal cation having a valence of at least 3. Naturally occurring polyelectrolytes which are suitable for forming the absorbent composition described by Ganslaw include anionic polyelectrolytes such as alginates, carrageenan, proteins, gum arabic, algin, agar, and gum ghatti.

The propensity of sodium alginate solutions to form spherical particles when dropped into a calcium chloride solution is known in the art of microencapsulation. See, for example, *Biomedical Applications of Microencapsulation,* Franklin Lim, Editor, (CRC Press, Inc., 1981) pp. 139–141; and *Microcapsule Processing and Technology,* Asaj Konda, (Marcel Dekker, Inc. 1979) pp. 59–63.

Unfortunately, known absorbent materials formed from phycocolloids have not proven particularly suited for use in the formation of absorbent products such as diapers, training pants, adult incontinence products, feminine care products, wound dressings and the like. As such, it is desirable to provide absorbent materials formed from phycocolloids which have a high degree of absorbency and which are suited for use in such absorbent products.

SUMMARY OF THE INVENTION

In one aspect, the present invention concerns a method for producing a water-swellable, substantially water-insoluble material. The method comprises the steps of preparing a first solution comprising water and from about 0.1 to about 25.0 weight percent, based on total weight of the first solution, of a water-soluble phycocolloid. The water-soluble phycocolloid is selected from the group consisting of algin and carrageenan. The first solution is added to a second solution containing an ion capable of rendering the water-soluble phycocolloid substantially water insoluble. The substantially water-insoluble phycocolloid is then recovered. Water present in the substantially water-insoluble phycocolloid is removed through solvent exchange and drying to produce a substantially water-insoluble, water-swellable material. In one preferred embodiment of the present invention, a gelation-retarding agent is added to either the first or second solution.

In another aspect, the present invention is directed to a water-swellable, substantially water-insoluble particle. The particle comprises an outer shell comprising a water-swellable, substantially water-insoluble phycocolloid. The phycocolloid is selected from the group consisting of algin and carrageenan. The outer shell defines an interior void. The interior void contains a phycocolloid.

DETAILED DESCRIPTION OF THE PREFERRED EMBODIMENTS

In one aspect, the present invention concerns a method for producing a water-swellable, substantially water-insoluble material. The method involves preparing a first solution comprising water and from about 0.1 to about 25.0 weight percent, desirably from about 0.5 to about 10.0 weight percent, and preferably from about 1.0 to about 5.0 weight percent, based on total weight of the first solution, of a water-soluble phycocolloid selected from the group consisting of algin and carrageenan. Any water-soluble algin or iota-carrageenan is believed suitable for use in the present invention. Examples of suitable algins include the alkali metal salts of alginic acid, hydroxyethyl alginate, hydroxypropyl alginate and carboxymethyl alginate. One preferred algin for use in the present invention is sodium alginate. Forms of iota-carrageenan suitable for use in the present invention include carboxymethyl carrageenan, hydroxyethyl carrageenan and hydroxypropyl carrageenan. Mixtures of algin and carrageenan may be used.

The first solution comprises water and the water-soluble phycocolloid. In addition to water, the first solution may comprise any other materials that do not deleteriously affect the process of the present invention, or the product formed thereby, to an unacceptable degree. For example, in addition to water, the first solution may comprise an organic solvent such as an alcohol. As a general rule, it is preferred that the first solution comprise at least about 50 weight percent water, beneficially at least about 75 weight percent water, more beneficially at least about 80 weight percent water, and preferably at least about 90 weight percent water. In one embodiment, the first solution comprises only water and the water-soluble phycocolloid.

In addition to the water-soluble phycocolloids described above, the first solution may contain up to 100 weight percent, based on the weight of the water-soluble phycocolloid present in the first solution, of an additional water-soluble polysaccharide or water-soluble synthetic polymer. Examples of other suitable water-soluble polysaccharides which may be included in the first solution include polysaccharide ethers such as carboxymethyl starch, carboxymethyl cellulose, hydroxypropyl cellulose, methyl cellulose and the like; and guar gum, gellan gum, locust bean gum, xantham gum and the like. In one preferred embodiment, the first solution comprises a combination of a water-soluble phycocolloid selected from the group consisting of algin and carrageenan and a water-soluble polysaccharide selected from the group consisting of carboxymethyl cellulose, carboxymethyl starch and guar gum. Examples of water-soluble synthetic polymers which may be included in the first solution include polyvinyl alcohol, polyvinyl pyrrolidone, poly(acrylic acid), poly(hydroxyethyl acrylate) and the like.

The first solution can be formed under any conditions which allow the water-soluble phycocolloid to form a solution. As used herein, reference to a solution refers to the situation wherein the phycocolloid dissolves in the water to form a true solution as well as the situation in which the phycocolloid swells to an extent that its original form cannot be determined, and the mixture flows like a true solution.

The molecular weight of algins and carrageenans are generally expressed in terms of viscosity ranges (low, medium and high). All viscosity ranges are believed suitable for use in the present invention. The viscosity of the first solution may be adjusted by changing the concentration of the phycocolloid in the solution.

A second solution containing an ion capable of rendering the water-soluble phycocolloid substantially water insoluble is prepared. Those skilled in the art will recognize a wide variety of ions which are capable of rendering water-soluble phycocolloids substantially water insoluble. Specifically, such ions are generally positively charged, divalent ions which react with the phycocolloid to render the phycocolloid substantially water insoluble. Positively charged ions capable of rendering the water-soluble phycocolloid substantially water insoluble include calcium, strontium, barium and mixtures thereof. When iota-carrageenan is employed as the water-soluble phycocolloid, aluminum ions are effective to render the water-soluble iota-carrageenan substantially water insoluble. In one preferred embodiment, the ion which renders the water-soluble phycocolloid substantially water insoluble is calcium.

The ion responsible for rendering the water-soluble phycocolloid substantially water insoluble is generally provided by placing an ionic compound into water, whereby the ionic compound ionizes to provide the ions. For example, calcium ions can be provided by dissolving calcium chloride in water. Similarly, aluminum ions can be provided by dissolving aluminum sulphate in water. Any ionic compound capable of providing the described ions is suitable for use in the present invention.

The concentration of the ions present in the second solution depends on the identity of the ions. As a general rule, the ion responsible for rendering the water-soluble phycocolloid substantially water insoluble will be present in a concentration of from about 0.1 weight percent to about 30.0 weight percent, preferably from about 0.5 weight percent to about 10.0 weight percent, and most preferably of from about 1.0 weight percent to about 5.0 weight percent, based on the total weight of the second solution. There is a wide degree of ion concentration possible for use in the second solution. This will be discussed in greater detail below.

The second solution comprises a liquid phase in which the ions are present. Any material in which ions can remain ionized is suitable for use in the present invention. Generally, the second solution will comprise water and the ions. It is, however, possible for the second solution to comprise other water-miscible liquids such as alcohols and ketones. The second solution can be formed under any condition in which the ions remain ionized.

The first solution is then added to the second solution. In order to form particles, including fibers, comprising the phycocolloid material, the first solution will generally be added to the second solution in a manner which causes discrete regions of the first solution to be formed within the second solution. Thus, for example, the first solution can be added to the second solution in a dropwise manner, whereby discrete regions of the first solution are formed within a continuous phase of the second solution. Alternatively, it may be possible to add the first solution to the second solution in a nondropwise manner, provided discrete regions of the first solution are formed within the second solution. For example, it may be possible to extrude a continuous stream of the first solution into the second solution. In such a case, it may be possible to produce fibers comprising the phycocolloid material.

The substantially water-insoluble, water-swellable material produced by the process of the present invention can be formed into particulate beadlike materials when the first solution is added to the second solution in a dropwise manner. For a given constant drop size, the more concentrated the first solution, the larger the resulting particle of phycocolloid material will be. Conversely, for the same drop size, a first solution containing a lower concentration of phycocolloid will produce a generally smaller particle. The viscosity of the first solution also affects particle formation. Specifically, if the viscosity of the first solution is too low, a drop of the first solution added to the second solution may lack sufficient surface tension forces to form a generally spherical shape. Similarly, if the viscosity of the first solution is too high, a drop of the first solution added to the second solution may gel (be rendered substantially water insoluble) before having sufficient time to form a generally spherical shape.

The beadlike particles produced according to the process of the present invention generally have a maximum cross-sectional dimension of from about 0.2 to about 4.0 millimeters and, preferably, of from about 0.5 to about 1.0 millimeter.

When the first solution is added to the second solution, the ions present in the second solution react with the phycocolloid present in the first solution to render the phycocolloid substantially water insoluble. Rendering the water-soluble phycocolloid insoluble is a time dependent and ion-concentration dependent reaction. Thus, the length of time for which the phycocolloid present in the first solution remains in contact with the second solution determines the degree of insolubilization of the phycocolloid. Similarly, the higher the ion concentration in the second solution, the shorter the period of time for which the phycocolloid of the first solution must remain in contact with the second solution to obtain a desired degree of insolubilization. When it is desired to produce a phycocolloid which is not only substantially water insoluble, but also generally water swellable, it is important that the insolubilization of the phycocolloid not proceed to too great a degree, or the phycocolloid will be nonwater swellable. The period of time for which the phycocolloid present in the first solution should remain in contact with the second solution is easily determined by experimentation and is dependent on solution temperature, ion concentration in the second solution, and the concentration of the phycocolloid in the first solution as well as the identity of the phycocolloid and ion employed. As a general, but nonlimiting rule, the phycocolloid present in the first solution should remain in contact with the ions present in the second solution for a period of time of from about 15 to about 180 seconds, preferably of from about 30 to about 120 seconds.

After the desired degree of insolubilization of the phycocolloid has occurred, the phycocolloid is removed from the second solution. Water present in the substantially water-insoluble but water-swellable phycocolloid is then removed through a solvent exchange. As used herein, reference to a solvent exchange refers to the situation wherein one or more components of a mixture is displaced (removed) by exposing the mixture to the action of a solvent in which the component to be removed is soluble. In the instant application, the water is removed from the phycocolloid through exposure to a liquid in which the water is soluble. For example, the solvent exchange can be conducted by exposing the water-containing phycocolloid to an organic solvent such as methanol, ethanol, ethylene glycol, acetone, methylethyl ketone, mixtures thereof and the like. Any liquid in which the water to be removed is soluble is believed suitable for use as a solvent exchange medium.

In a preferred embodiment of the present invention, either the first solution or the second solution contains from about 0.1 to about 25.0 weight percent, beneficially from about 0.5 to about 10 weight percent, and preferably from about 1.0 to about 5.0 weight percent, based on total weight of the first or second solution, of a gelation-retarding agent. As used herein, reference to a gelation-retarding agent refers to a material which is capable of competing with or combining with the ions present in the second solution to prevent or retard the ions from rendering the water-soluble phycocolloid substantially water insoluble. Some of the gelation-retarding agents are also known as sequestering agents. As a general rule, the gelation-retarding agent functions by competing with the phycocolloid present in the first solution such that the ions present in the second solution are unable or slower to render all of the water-soluble phycocolloid substantially water insoluble. Obviously, the concentration of gelation-retarding agent necessary to achieve this function depends on the concentration of the ions in the second solution.

Suitable gelation-retarding agents include citric acid; salts, such as sodium chloride, sodium sulfate, sodium acetate, and the like; and phosphates, such as hexametasodium phosphate, trisodium phosphate, and the like; and mixtures thereof. Other gelation-retarding agents are known to those skilled in the art and are suitable for use in the present invention. For example, when the gelation-retarding agent comprises a sodium salt present in the first solution and the phycocolloid comprises sodium alginate, the second solution may suitably comprise a calcium ion. The calcium ion can render the sodium alginate substantially water insoluble by exchanging with the sodium ion of the sodium alginate to produce calcium alginate. The presence of the sodium salt retards the conversion of sodium alginate to calcium alginate by competing with the calcium ions for the available sites on the sodium alginate.

When the gelation-retarding agent comprises a sequestering agent, such as hexametasodium phosphate, the gelation-retarding agent functions by combining with the ion present in the second solution. That is, for example, the affinity of hexametasodium phosphate to complex with the calcium is greater than the affinity for calcium to replace sodium ions present on the sodium alginate.

The water-swellable, substantially water-insoluble material produced without the addition of a gelation-retarding agent, or when the gelation-retarding agent is present in the second solution, is generally a solid particle or fiber. This is because essentially the entire amount of phycocolloid present in the first solution, when it is added to the second solution, becomes crosslinked and, thus, rendered substantially water insoluble. The presence of the gelation-retarding agent in the second solution retards the rate of crosslinking of the phycocolloids. Thus, a more controlled process is possible.

In contrast, when the gelation-retarding agent is present in the first solution, the particles or fibers produced by the process of the present invention define an interior void. Such particles are known as microballoons and such fibers as hollow fibers. Applicant has discovered that such hollow structures can form naturally without the use of blowing agents or annular die tips.

Without intending to be bound thereby, Applicant hypothesizes that the presence of a gelation-retarding agent in the first solution prevents that water-soluble phycocolloid present in the interior of the discrete area of first solution present in the second solution from becoming crosslinked to a sufficient degree to render it water insoluble. That is, due to the presence of the gelation-retarding agent, the water-soluble phycocolloid present in the interior of the, for example, drop of first solution added to the second solution does not become crosslinked by the ions present in the second solution. Nonetheless, due to the higher ion concentration present on the outer surface of the drop of first solution, the phycocolloid located generally nearer the interface of the first solution and second solution becomes ionically crosslinked and thus water insoluble.

When such phycocolloid particles are removed from the second solution, and subjected to a solvent exchange, the water present in the interior of the particles is replaced with the solvent used to accomplish the solvent exchange. At this point the phycocolloid present in the interior of the particles is precipitated out of solution. When the solvent is a material such as ethanol, methanol, acetone, and the like, upon exposure to the air, the solvent evaporates, thus, leaving the interior of the particle hollow, such that the outer crosslinked shell of phycocolloid defines an interior void. The phycocolloid originally present in the interior void is still present in the interior void as a solid particle. Such phycocolloid is water swellable, but water insoluble, as the protective effect of the gelation-retarding agent is only temporary. During the solvent exchange, the gelation-retarding agent diffuses out of the particle along with the water.

In another aspect, the present invention concerns a water-swellable, substantially water-insoluble particle. The particle comprises an outer shell comprising a water-swellable, substantially water-insoluble phycocolloid selected from the group consisting of algin and carrageenan. The outer shell defines an interior void. The interior void defined by the outer shell contains a phycocolloid. The phycocolloid is water swellable, but water insoluble. The algins and carrageenans suitable for use in forming the outer shell are the same as set forth above in connection with forming the first solution. Similarly, the outer shell may comprise, in addition to the algin and carrageenan, other suitable water-swellable, substantially water-insoluble polysaccharides and/or synthetic polymers. Such suitable polysaccharides and synthetic polymers are, again, the same as those set forth above in connection with the formation of the first solution. It is preferred that the outer shell comprise at least about 50 weight percent of the phycocolloid with up to about 50 weight percent of a polysaccharide or synthetic polymer, based on total weight of the outer shell. It is specifically preferred that the phycocolloid forming the outer shell be selected from the group consisting of the divalent metal salts of alginic acid and the di and trivalent metal salts of iota-carrageenan.

The described water-swellable, substantially water-insoluble particles are suitably formed by the process set forth above when the first solution comprises a gelation-retarding agent. Thus, as can be appreciated by those skilled in the art, the water-soluble phycocolloids present in the interior void may be the same phycocolloids from which the outer shell is formed and may be water soluble or water insoluble and may or may not contain the same ionic crosslinker.

The substantially water-insoluble, water-swellable particles of the present invention are suitably employed as absorbent materials in the formation of absorbent products such as diapers, training pants, adult incontinent products, feminine care products, wound dressings, wipes, and the like.

EXAMPLES

Example 1

Absorbent beadlike particles were made by the process of the present invention wherein the first solution comprised water and 1–2 weight percent, based on total weight of the first solution, of a phycocolloid selected from the group consisting of sodium alginate (Na Alginate), commercially available from Colony Import and Export Corporation under the trade designation Sodium Alginate S-1100; carboxymethyl sodium alginate (CM Na Alginate) formed by carboxymethylating sodium alginate with monochloroacetic acid; iota-carrageenan (carrageenan), commercially available from Hercules, Inc. under the trade designation Genugel; and mixtures of Na Alginate and carrageenan. First solutions comprising water and 1–2 weight percent, based on total weight of the first solution, of a mixture of Na Alginate or carrageenan with carboxymethyl cellulose (CMC), commercially available from Aqualon under the trade designation Cellulose Gum Type 7HCF, carboxymethyl starch (CMS), commercially available from A. E. Staley Mfg. Co. under the trade designation C3-450, guar gum, commercially available from Colony Import and Export Corporation under the trade designation Guar Gum FG-HV, or dextrin, commercially available from A. E. Staley Mfg. Co. under the trade designation Stadex®, were also prepared. The first solution optionally comprised a gelation-retarding agent selected from the group consisting of $NaH_2PO_4$ and $(NaPO_3)_6$. The exact composition of the first solution is set forth in Table 1.

The first solution was added, in a dropwise manner, to a stirred container of a second solution. A sufficient quantity of the second solution was present to allow free movement of the drops of first solution. The drops contained approximately 0.1 milliliter of the first solution. The second solution comprised water and an ionic compound selected from the group consisting of calcium chloride, sodium phosphate monobasic, barium chloride, chitosan, aluminum sulfate and mixtures thereof. The exact composition of the second solution is set forth in Table 1.

The drops of first solution were allowed to remain in the second solution for a period of from 30 seconds to 60 minutes as set forth in Table 1 (cure time). The particles were then removed from the second solution and the water present therein removed by solvent exchange with acetone by placing the particles in acetone for a period of up to 60 minutes. The particles were then removed from the acetone and allowed to air dry for four hours.

The absorbent capacity of the particles was then determined by placing a known quantity (in grams) of the particles in an excess of an aqueous solution containing 1 weight percent sodium chloride for a period of time of from about 1 hour to about 19 hours. The particles were then removed from the sodium chloride solution and weighed to determine the amount, in grams, of sodium chloride solution absorbed per gram of absorbent particles. The period of time for which the particles were allowed to remain in contact with the sodium chloride solution and the absorbency of the particles on a gram per gram basis are set forth in Table 1. As indicated in Table 1, for certain samples, the absorbency was determined in an aqueous solution containing 1 weight percent sodium chloride and 1 weight percent sodium hypophosphate or in distilled water.

TABLE 1

| Sample No. | First Solution (wt. %) | Second Solution (wt. %) | Cure time[1] (min) | Absorbent Capacity (g/g) | Test[2] Time (hr) |
|---|---|---|---|---|---|
| 1 | 1% Na Alginate | 2.5% $CaCl_2$/10% $NaH_2PO_4$ | 2 | 15 | 1 |
| 2 | 1% Na Alginate | 2% $CaCl_2$/4% $NaH_2PO_4$ | 5 | 20 | 4 |
| 3 | 1% Na Alginate | 2% $CaCl_2$/4% $NaH_2PO_4$ | 5 | 39[3] | 5 |
| 4 | 1% Na Alginate | 2% $CaCl_2$/4% $NaH_2PO_4$ | 0.5 | 50 | 4 |
| 5 | 1% Na Alginate | 2% $CaCl_2$ | 0.5 | 24 | 5 |
| 6 | 1% Na Alginate | 2% $CaCl_2$ | 0.5 | 11[4] | 3 |
| 7 | 1% Na Alginate/4% $NaH_2PO_4$ | 2% $CaCl_2$ | 2 | 18 | 3 |
| 8 | 1% Na Alginate/4% $NaH_2PO_4$ | 2% $CaCl_2$ | 2 | 25 | 19 |
| 9 | 1% Na Alginate/1% $(NaPO_3)_3$ | 2% $CaCl_2$ | 1 | 12 | 2 |
| 10 | 1% Na Alginate/1% $(NaPO_3)_3$ | 2% $CaCl_2$ | 1 | 17 | 19 |
| 11 | 1% Na Alginate | 1% $CaCl_2$ | 0.5 | 43 | 4 |
| 12 | 1% Na Alginate | 1% $CaCl_2$ | 1 | 36 | 4 |
| 13 | 1% Na Alginate | 1% $CaCl_2$ | 2 | 37 | 4 |
| 14 | 1% Na Alginate | 1% $CaCl_2$ | 4 | 29 | 4 |
| 15 | 1% Na Alginate | 1% $BaCl_2$ | 0.5 | 15 | 5 |
| 16 | 1% Na Alginate | 1% Chitosan | 60 | 88 | 6 |
| 17 | 1% Na Alginate | 1% Chitosan/0.1% $CaCl_2$ | 5 | 39 | 1.5 |
| 18 | 1% Na Alginate | 1% Chitosan/0.1% $CaCl_2$ | 5 | 49 | 2.5 |
| 19 | 1% Na Alginate | 1% Chitosan/0.1% $CaCl_2$ | 5 | 56 | 5 |
| 20 | 1% Na Alginate | 0.1% $CaCl_2$ | 5 | 41 | 1.5 |
| 21 | 1% Na Alginate | 0.1% $CaCl_2$ | 5 | 47 | 2.5 |
| 22 | 1% Na Alginate | 0.1% $CaCl_2$ | 5 | 51 | 5 |
| 23 | 1.5% CM Na Alginate | 1% $CaCl_2$ | 0.5 | 21 | 5 |
| 24 | 2% Carrageenan | 2% $CaCl_2$ | 45 | 12 | 1 |
| 25 | 2% Carrageenan | 2% $CaCl_2$ | 45 | 26 | 6 |

TABLE 1-continued

| Sample No. | First Solution (wt. %) | Second Solution (wt. %) | Cure time[1] (min) | Absorbent Capacity (g/g) | Test[2] Time (hr) |
|---|---|---|---|---|---|
| 26 | 2% Carrageenan | 1% $CaCl_2$/1% $Al_2(SO_4)_3$ | 45 | 20 | 2 |
| 27 | 2% Carrageenan | 1% $CaCl_2$/1% $Al_2(SO_4)_3$ | 45 | 29 | 4 |
| 28 | 2% Carrageenan | 1% $CaCl_2$/1% $Al_2(SO_4)_3$ | 45 | 4[4] | 3 |
| 29 | 2% Carrageenan | 2% $Al_2(SO_4)_3$ | 10 | 12 | 3.5 |
| 30 | 2% Carrageenan | 1% Chitosan/0.1% $CaCl_2$ | 150 | 40 | 1.5 |
| 31 | 2% Carrageenan | 1% Chitosan/0.1% $CaCl_2$ | 150 | 52 | 2.5 |
| 32 | 1% Na Alginate/Carrageenan (50/50) | 2% $Al_2(SO_4)_3$ | 5 | 26 | 3.5 |
| 33 | 1% Na Alginate/Carrageenan (50/50) | 2% $CaCl_2$ | 45 | 37 | 2 |
| 34 | 1% Na Alginate/Carrageenan (50/50) | 2% $CaCl_2$ | 45 | 48 | 4 |
| 35 | 1.25% Na Alginate/Carrageenan (80/20) | 1% $BaCl_2$ | 0.5 | 22 | 5 |
| 36 | 1% Na Alginate/Guar Gum (67/33) | 2% $CaCl_2$ | 1 | 20 | 3.5 |
| 37 | 1% Na Alginate/CMC (50/50) | 1% $CaCl_2$ | 2 | 20 | 1 |
| 38 | 1% Na Alginate/CMC (50/50) | 1% $CaCl_2$ | 2 | 35 | 4 |
| 39 | 1% Na Alginate/CMC (50/50) | 1% $CaCl_2$ | 2 | 40 | 6 |
| 40 | 1% Na Alginate/CMS (50/50) | 1% $CaCl_2$ | 1 | 24 | 1 |
| 41 | 1% Na Alginate/CMS (50/50) | 1% $CaCl_2$ | 1 | 34 | 4 |
| 42 | 1% Na Alginate/CMS (50/50) | 1% $CaCl_2$ | 1 | 37 | 6 |
| 43 | 1% Na Alginate/Dextrin (50/50) | 1% $CaCl_2$ | 0.25 | 37 | 6 |
| 44 | 1% Carrageenan/CMC (50/50) | 1% $Al(SO_4)_3$ | 1 | 21 | 0.5 |
| 45 | 1% Carrageenan/CMC (50/50) | 1% $Al(SO_4)_3$ | 1 | 34 | 5 |
| 46 | 1% Carrageenan/CMC (50/50) | 1% $Al(SO_4)_3$ | 1 | 42 | 7 |
| 47 | 1% Carrageenan/CMS (50/50) | 1% $Al(SO_4)_3$ | 10 | 7 | 0.5 |
| 48 | 1% Carrageenan/CMS (50/50) | 1% $Al(SO_4)_3$ | 10 | 22 | 5 |
| 49 | 1% Carrageenan/CMS (50/50) | 1% $Al(SO_4)_3$ | 10 | 25 | 7 |
| 50 | 1% Carrageenan/Guar Gum (67/33) | 1% $CaCl_2$ | 75 | 22 | 1 |
| 51 | 1% Carrageenan/Guar Gum (67/33) | 1% $CaCl_2$ | 75 | 44 | 4 |

1. Time (in minutes) drops of first solution were allowed to remain in second solution.
2. Time (in hours) dried particle was allowed to remain in contact with the aqueous 1% NaCl solution.
3. Tested in aqueous solution comprising 1% NaCl and 1% $NaH_2PO_4$
4. Tested in distilled water instead of the aqueous 1% NaCl solution As can be seen from reference to Table 1, both algins and carrageenan are capable of forming absorbent particles, according to the method of the present invention, which particles have a high absorbent capacity in a saline solution. Further, a wide variety of ions are suitable for use in the second solution. Mixtures of algin and carrageenan are also suitable for forming absorbent particles according to the present invention. Further, the algin and carrageenan can be combined with other water-soluble polysaccharides to produce absorbent particles according to the present invention. For example, with reference to Samples 37–42 and 44–49, Applicant notes that neither carboxymethyl cellulose nor carboxymethyl starch form absorbent particles according to the method of the present invention. However, when the carboxymethyl cellulose and carboxymethyl starch are combined with an algin or carrageenan, absorbent particles according to the present invention are formed through the described method.

Example 2

In a similar manner, particles of a water-swellable, substantially water-insoluble absorbent material were made which define an interior void. These hollow particles were formed by adding a gelation-retarding agent to the first solution according to the following method. A first solution was formed from water and 2 weight percent, based on total first solution weight, of a sodium alginate, commercially available from Colony Import and Export Corporation, under the trade designation Sodium Alginate S-1100. To the first solution was then added 0–8 weight percent, based on total weight of the first solution, of a gelation-retarding agent. The gelation-retarding agents employed were either hexametasodium phosphate $(NaPO_3)_6$, sodium chloride (NaCl), or sodium acetate $(NaC_2H_3O_2)$. As in Example 1, the first solution was then dripped into a second solution comprising water and 1 weight percent calcium chloride ($CaCl_2$). The first solution was dripped into the second solution for a period of from 0.5 to 2 minutes (drip time) and the particles were allowed to harden (cure) in the second solution for a period of time from 0.5 to 3 minutes. The particles were then rinsed in water and transferred to anhydrous methanol. The solvent exchange in anhydrous methanol was allowed to continue for up to four hours.

The particles were then removed from the methanol and allowed to air dry. The absorbent capacity of the particles was then determined in an aqueous solution comprising 1 weight percent sodium chloride by floating the particles in an excess of the saline solution for 5 hours. The exact formation conditions, the absorbent capacity, and the size of the hollow particles formed are set forth in Table 2.

TABLE 2

| Sample No. | First Solution (wt. %) | Gelation-Retarding Agent | Second Solution (wt. %) | Drip time (min) | Cure time (min) | Absorbent Capacity (g/g) | Size (mm) |
|---|---|---|---|---|---|---|---|
| 52 | 2% Na Alginate | 2% $(NaPO_3)_6$ | 1% $CaCl_2$ | 2 | 3 | 8.8 | 2.3–2.8 |
| 53 | 2% Na Alginate | 4% $(NaPO_3)_6$ | 1% $CaCl_2$ | 1 | 1 | dissolved | 3.0–3.5 |
| 54 | 2% Na Alginate | None | 1% $CaCl_2$ | 0.5 | 0.5 | 14 | solid particle |
| 55 | 2% Na Alginate | 8% NaCl | 1% $CaCl_2$ | 1 | 2 | 22.8 | 1.8–2.6 |
| 56 | 2% Na Alginate | 4% $CH_3COONa$ | 1% $CaCl_2$ | 1 | 2 | 22.5 | 1.3–1.8 |

The presence of the gelation-retarding agent in the first solution in Samples 52, 55, and 56 resulted in the production of a hollow, absorbent particle having a desirable absorbent capacity. Sample 53 was soluble instead of absorbent, indicating insufficient curing time in the second solution.

Example 3

Absorbent particles according to the present invention were produced from a first solution comprising 2 weight percent of the sodium alginate employed in Example 2 and 2 weight percent (based on total first solution weight) of hexametasodium phosphate. As in Example 2, the first solution was dripped into a second solution comprising 1 weight percent of calcium chloride. The first solution was dripped into the second solution over a period of 1 minute and the particles were allowed to cure in the second solution for 1 minute before being removed. After removal from the second solution, a first quantity of particles was placed in anhydrous methanol for solvent exchange, a second quantity was placed in acetone for solvent exchange, and a third quantity was allowed to air dry. The particles which were solvent exchanged in methanol produced hollow spheres having an absorbent capacity of 12 grams per gram after 4 hours in an aqueous solution containing I weight percent of sodium chloride. The particles that were solvent exchanged in acetone produced hollow flakes having an absorbent capacity of 19.8 grams per gram after four hours in an aqueous solution containing 1 weight percent sodium chloride. The particles which were allowed to air dry produced solid particles having an absorbent capacity of 9.1 grams per gram after four hours in an aqueous solution containing I weight percent sodium chloride.

While the invention has been described in detail with respect to specific embodiments thereof, it will be appreciated that those skilled in the art, upon obtaining an understanding of the foregoing, may readily conceive of alterations to, variations of, and equivalents to these embodiments. Accordingly, the scope of the present invention should be assessed as that of the appended claims and any other equivalents thereto.

What is claimed is:

1. A water-swellable, water-insoluble particle defining an interior void produced by a method comprising the following steps:

preparing a first solution comprising water, a gelation-retarding agent, and from about 0.1 to about 25.0 weight percent, based on total weight of the first solution, of a water-soluble phycocolloid selected from the group consisting of algin and carrageenan;

adding said first solution to a second solution containing an ion capable of rendering said water-soluble phycocolloid water insoluble whereby particles are formed;

recovering said particles; and removing water present in said particles through a solvent exchange to produce a water-swellable, water-insoluble particle defining an interior void containing the phycocolloid as a solid particle.

2. An absorbent product, said absorbent product comprising a water-swellable, substantially water-insoluble particle, said particle comprising:

an outer shell comprising a water-swellable, substantially water-insoluble phycocolloid selected from the group consisting of algin and carrageenan; and an interior void defined by said outer shell, said void containing the phycocolloid as a solid particle.

3. The absorbent product according to claim 2 wherein said water-insoluble phycocolloid is selected from the group consisting of the divalent metal salts of alginic acid and the di- and trivalent metal salts of iota-carrageenan.

4. The absorbent product according to claim 3 wherein said outer shell comprises said water-insoluble phycocolloid and up to about 50 weight percent, based on the total weight of the outer shell, of a polysaccharide or synthetic polymer.

* * * * *